United States Patent
Benn et al.

(10) Patent No.: US 9,439,715 B2
(45) Date of Patent: Sep. 13, 2016

(54) ELECTROSURGICAL INSTRUMENT

(75) Inventors: Christopher Charles Benn, Bristol (GB); Robert C. Humble, Monmouthshire (GB); David W. Morris, Rhondda (GB); Michael David Newton, Newport (GB); Andrew John Ford, North Somerset (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1147 days.

(21) Appl. No.: 13/016,273

(22) Filed: Jan. 28, 2011

(65) Prior Publication Data

US 2011/0190762 A1 Aug. 4, 2011

Related U.S. Application Data

(60) Provisional application No. 61/282,381, filed on Feb. 1, 2010.

(30) Foreign Application Priority Data

Feb. 1, 2010 (GB) .................................. 1001644.2

(51) Int. Cl.
- *A61B 18/12* (2006.01)
- *A61B 18/14* (2006.01)
- *A61B 18/00* (2006.01)

(52) U.S. Cl.
CPC ...... *A61B 18/14* (2013.01); *A61B 2018/00589* (2013.01); *A61B 2018/00601* (2013.01); *A61B 2018/124* (2013.01); *A61B 2018/1467* (2013.01)

(58) Field of Classification Search
CPC .................... A61B 18/14; A61B 2018/00589; A61B 2018/00601; A61B 2018/124; A61B 2018/1467
USPC ............................................. 606/27, 34, 41
See application file for complete search history.

(56) References Cited

U.S. PATENT DOCUMENTS

| | | | | |
|---|---|---|---|---|
| 4,682,596 A | * | 7/1987 | Bales ...................... | A61B 18/14 606/39 |
| 5,192,280 A | * | 3/1993 | Parins ............................ | 606/48 |

(Continued)

FOREIGN PATENT DOCUMENTS

| | | |
|---|---|---|
| GB | 2 447 767 | 9/2008 |
| JP | 2004-160083 | 10/2004 |

(Continued)

OTHER PUBLICATIONS

International Search Report issued in corresponding International Application No. PCT/GB2011/000070, Date of Mailing: Apr. 12, 2011.

(Continued)

*Primary Examiner* — Daniel Fowler
(74) *Attorney, Agent, or Firm* — Nixon & Vanderhye PC (57) ABSTRACT

An electrosurgical instrument is provided for the treatment of tissue, the instrument comprising an instrument shaft (10) having a longitudinal axis, and an electrode assembly at one end of the shaft. The electrode assembly comprises first and second active electrodes (11), (14) and at least one return electrode (25), the electrodes being electrically insulated one from another by means of one or more insulation members (12). The first and second active electrodes (11, 14) each have an exposed surface for treating tissue, the exposed surface (19) of the first active electrode being such as to treat tissue disposed laterally of the longitudinal axis at a first radial position with respect to the instrument shaft. The exposed surface (15) of the second active electrode is such as to treat tissue disposed laterally of the longitudinal axis at a second radial position with respect to the instrument shaft. The instrument has a first set of connections by which the first active electrode (11) can be placed in circuit with the return electrode (25), and a second set of connections by which the second active electrode (14) can be placed in circuit with the return electrode (25).

22 Claims, 6 Drawing Sheets

(56) References Cited

U.S. PATENT DOCUMENTS

| | | | |
|---|---|---|---|
| 5,217,457 A * | 6/1993 | Delahuerga et al. | 606/42 |
| 5,462,545 A * | 10/1995 | Wang et al. | 606/41 |
| 5,697,909 A * | 12/1997 | Eggers et al. | 604/114 |
| 5,769,791 A * | 6/1998 | Benaron | G01N 21/4795 600/473 |
| 6,004,319 A | 12/1999 | Goble | |
| 6,152,923 A * | 11/2000 | Ryan | 606/51 |
| 6,293,942 B1 | 9/2001 | Goble et al. | |
| 6,379,350 B1 * | 4/2002 | Sharkey et al. | 606/41 |
| 6,832,998 B2 | 12/2004 | Goble | |
| 6,966,907 B2 | 11/2005 | Goble | |
| 7,048,734 B1 * | 5/2006 | Fleischman et al. | 606/42 |
| 7,052,496 B2 * | 5/2006 | Yamauchi | 606/51 |
| 7,195,630 B2 * | 3/2007 | Ciarrocca | 606/48 |
| 2003/0125732 A1 | 7/2003 | Goble | |
| 2004/0024398 A1 * | 2/2004 | Hovda et al. | 606/41 |
| 2007/0049921 A1 | 3/2007 | Konishi et al. | |
| 2008/0234673 A1 * | 9/2008 | Marion | A61B 18/1482 606/45 |
| 2009/0048592 A1 | 2/2009 | Thomas et al. | |

FOREIGN PATENT DOCUMENTS

| | | |
|---|---|---|
| JP | 2008-295905 | 11/2008 |
| WO | 99/00060 A | 1/1999 |
| WO | WO 2007/092101 | 8/2007 |
| WO | 2010/006068 A2 | 1/2010 |

OTHER PUBLICATIONS

Written Opinion issued in corresponding International Application No. PCT/GB2011/000070, Date of Mailing: Apr. 12, 2011.
Search Report issued in UK Patent Application No. 1001644.2, date of search May 24, 2010.
Japanese Office Action Patent Application No. 2012-550505; dated Sep. 29, 2014.
English language translation of Japanese Office Action for corresponding Japanese Patent Application No. 2012-550505; dated Sep. 29, 2014.
Examination Report No. 1, Australian Patent Application No. 2011-209571; dated Feb. 2, 2015.
Examination Report, UK Patent Application No. GB 1001644.2; dated Jul. 2, 2015.

\* cited by examiner

ELECTROSURGICAL INSTRUMENT

This application claims priority to United Kingdom Application No. 1001644.2, filed 1 Feb. 2010 and claims the benefit of U.S. Provisional Application No. 61/282,381, filed 1 Feb. 2010, the entire contents of which are hereby incorporated by reference.

This invention relates to an electrosurgical instrument for the treatment of tissue, and to an electrosurgical system including such an instrument and an electrosurgical generator. Such systems are commonly used for the vaporisation and/or coagulation of tissue in surgical intervention, most commonly in "keyhole" or minimally invasive surgery, but also in "open" surgery.

It is often the case that during a surgical procedure the surgeon is required to remove a first instrument and insert a second instrument, in order to achieve a particular tissue effect. The present invention attempts to provide a surgical instrument that can be used in more than one manner, so as to reduce the number of times that an alternative instrument needs to be used.

Accordingly, an electrosurgical instrument is provided for the treatment of tissue, the electrosurgical instrument including an instrument shaft having a longitudinal axis and an electrode assembly at one end of the shaft, the electrode assembly comprising first and second active electrodes, and one or more return electrodes, each of the electrodes being electrically insulated one from another by means of one or more insulation members, the first and second active electrodes each having an exposed surface for treating tissue, the first and second active electrodes each having a different characteristic, the exposed surface of the first active electrode being such as to treat tissue disposed laterally of the longitudinal axis at a first radial position with respect to the instrument shaft, the exposed surface of the second active electrode being such as to treat tissue disposed laterally of the longitudinal axis at a second radial position with respect to the instrument shaft, the first and second radial positions being separated by at least 30°, the instrument having a first set of connections by which the first active electrode can be placed in circuit with one of the one or more return electrodes such that in use a current path is established between the first active electrode and at least one return electrode, and a second set of connections by which the second active electrode can be placed in circuit with one of the one or more return electrodes such that in use a current path is established between the second active electrode and at least one return electrode.

By providing the first and second active electrodes with a different characteristic, the electrosurgical instrument of the present invention provides a first active electrode which is optimised for tissue vaporisation, and a second active electrode which is optimised for tissue coagulation. As the first and second active electrodes are located at different radial positions around the shaft of the instrument, the user of the instrument can readily select the electrode to use, simply by rotating the instrument.

According to a convenient arrangement, the first and second radial positions are separated one from another by at least 45°, preferably by at least 90°, and conceivably to by approximately 180°. This means that the user of the instrument rotates the instrument shaft by a known amount in order to switch between the first and second active electrodes being in the correct position for use.

As stated above, the first active electrode is optimised for tissue vaporisation and the second active electrode is optimised for tissue coagulation. One way in which this can be achieved is by making the distance between the first active electrode and the nearest return electrode less than that between the second active electrode and the nearest return electrode. With a shorter distance between the active and return electrodes when the first active electrode is employed, the bipolar electrode pair is more likely to fire up into a tissue cutting mode. Conversely, with a longer distance between the active and return electrodes when the second active electrode is employed, the bipolar electrode pair has a separation sufficient to create a larger area of coagulated tissue.

Alternatively or additionally, another way of optimising the first and second active electrodes for their particular tasks is by ensuring that the surface area of the first active electrode is less than that of the second active electrode. A smaller electrode such as the first active electrode will create a higher current concentration, and will hence fire up more easily into tissue cutting mode. Similarly, a larger area electrode such as the second active electrode will have a surface area to create a substantial area of coagulated tissue, as well as being less likely to fire up into tissue cutting mode. Thus a higher voltage can be applied to a large area electrode without the risk of the coagulation electrode switching over into undesired tissue cutting activity.

Alternatively or additionally, another way of optimising the first and second active electrodes for their particular tasks is by ensuring that the shape of the first active electrode is different from that of the second active electrode. A more pointed or irregular structure for the first active electrode will promote voltage concentration about the points of irregularity, and encourage tissue cutting. Conversely, a smooth or flat second active electrode will discourage tissue cutting activation, and promote the uniform coagulation of tissue. Whichever combination of characteristics is employed, the first and second active electrodes can be designed to be well suited to their intended task, as opposed to the compromise necessary where a single electrode is designed to perform multiple tasks. Notwithstanding the bespoke nature of the tissue treatment electrodes, both tissue vaporisation and tissue coagulation can be performed from a single instrument, merely by rotating the instrument to bring the alternate electrode into position. Thus it is not necessary to remove the instrument and insert a second instrument, in order to achieve both cutting and coagulation of tissue.

According to a convenient arrangement, at least a portion of the one or more return electrodes is set back axially with respect to the first active electrode, and preferably with respect to the second active electrode as well. This is conveniently achieved by positioning the first and second active electrodes towards the extreme distal end of the instrument. Conveniently, at least one of the return electrodes is in the form of a radial band around the instrument shaft, typically a metallic sheath present on the instrument shaft.

Conveniently, the exposed tissue treatment surface of the first active electrode is substantially planar, and preferably the exposed tissue treatment surface of the second active electrode is substantially planar as well. By providing substantially planar electrode surfaces, the instrument can easily be rotated to bring either electrode adjacent tissue to be treated.

The instrument preferably also includes a suction lumen extending along the length of the shaft. Conveniently, the first active electrode is provided with at least one aperture in communication with the suction lumen. Conceivably the second active electrode is also provided with at least one aperture in communication with the suction lumen, although this is not as important as the second active electrode is solely performing tissue coagulation. The suction lumen can be used to aspirate tissue debris and other vaporised matter from the vicinity of the electrodes. Conceivably, the lumen could additionally or alternatively be used for the supply of fluid to the distal end of the instrument.

According to a convenient arrangement, the one or more return electrodes comprises a first return electrode and a second return electrode, and the first set of connections are such that the first active electrode can be placed in circuit with the first return electrode such that in use a current path is established between the first active electrode and the first return electrode, and the second set of connections are such that the second active electrode can be placed in circuit with the second return electrode such that in use a current path is established between the second active electrode and the second return electrode. In this construction, each of the first and second active electrodes has its own particular return electrode, allowing the positioning of the electrodes on the instrument shaft to be optimised.

According to a further aspect of the invention there is provided an electrosurgical system including an electrosurgical instrument and an electrosurgical generator, the electrosurgical instrument including an instrument shaft having a longitudinal axis and an electrode assembly at one end of the shaft, the electrode assembly comprising first and second active electrodes, and one or more return electrodes, each of the electrodes being electrically insulated one from another by means of one or more insulation members, the first and second active electrodes each having an exposed surface for treating tissue, the exposed surface of the first active electrode being such as to treat tissue disposed laterally of the longitudinal axis at a first radial position with respect to the instrument shaft, the exposed surface of the second active electrode being such as to treat tissue disposed laterally of the longitudinal axis at a second radial position with respect to the instrument shaft, the first and second radial positions being separated by at least 30°, the instrument having a first set of connections by which the first active electrode can be placed in circuit with one of the one or more return electrodes such that in use a current path is established between the first active electrode and at least one return electrode, and a second set of connections by which the second active electrode can be placed in circuit with one of the one or more return electrodes such that in use a current path is established between the second active electrode and at least one return electrode, the electrosurgical generator including a source of radio frequency energy capable of producing either a coagulating RF waveform or a cutting RF waveform, and first and second output connections connected to the first and second active electrodes respectively and a third output connection connected to the one or more return electrodes of the electrosurgical instrument, the generator further including a switch means, and a switching circuit, the switching circuit being such that when a cutting RF waveform is selected, the switching circuit directs the cutting RF waveform between the first and third output connections and hence the first active electrode and at least one return electrode, and when a coagulating RF waveform is selected, the switching circuit directs the coagulating RF waveform between the second and third output connections and hence the second active electrode and at least one return electrode.

As before, the first and second active electrodes each have a different characteristic, for providing a first active electrode which is optimised for tissue vaporisation, and a second active electrode which is optimised for tissue coagulation. The electrosurgical system includes the switch means by which the surgeon can select either the cutting RF waveform or coagulating RF waveform modes of operation. Conveniently, the switch means comprises a footswitch, although as an alternative the switch means conceivably comprises a handswitch carried on the electrosurgical instrument. Alternatively, the switch means can be located on the generator. The switch means activates the switching circuit, which is conveniently a part of the generator, although as an alternative the switching circuit is conceivably a part of the electrosurgical instrument.

In a first arrangement, the generator and electrosurgical instrument are such that the instrument is designed to be operated in a conductive fluid, with the conductive fluid completing the current path between the electrodes. This means that the system operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage setting used by the generator are such that the conductive fluid surrounding the electrodes is vaporised when the electrosurgical instrument is operated in its cutting mode.

Alternatively, the generator and electrosurgical instrument are such that the instrument is designed to be operated in a dry-field environment, with the electrodes being in direct contact with the tissue to be treated, and with the tissue completing the current path therebetween. An example of this type of electrosurgical system is given in our earlier U.S. Pat. No. 6,832,998. The power and voltage settings used by the generator are generally lower than in underwater electrosurgical systems, as the electrodes contact the tissue directly and there is no need to form a pocket of vaporised saline surrounding the electrode.

The invention will now be further described, by way of example only, with reference to the accompanying drawings, in which.

Figure 1:
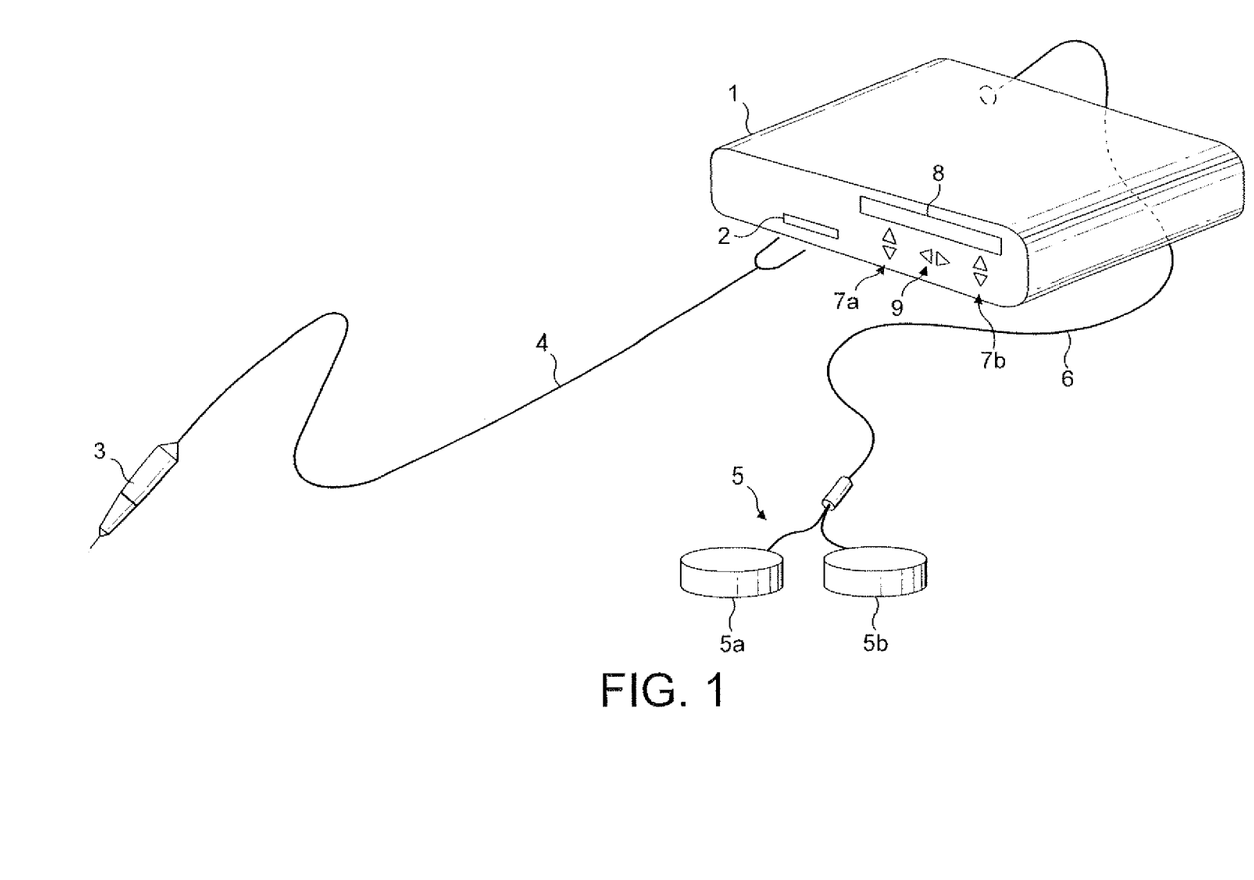
FIG. 1 is a schematic diagram of an electrosurgical system in accordance with the present invention.
Figure 2:
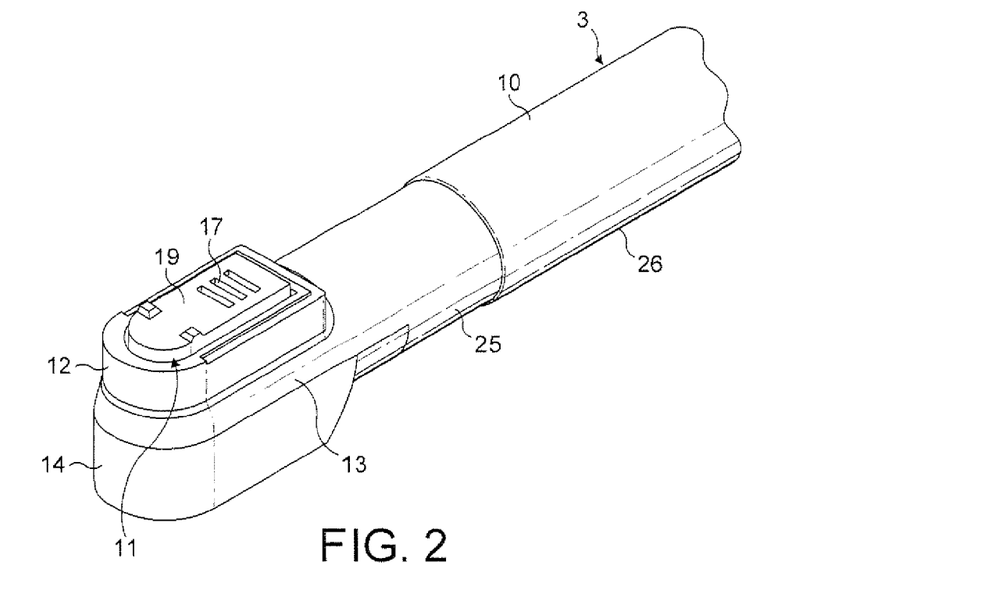
FIG. 2 is a perspective view of an electrosurgical instrument in accordance with the present invention and capable of being used in the system of FIG. 1.
Figure 3:
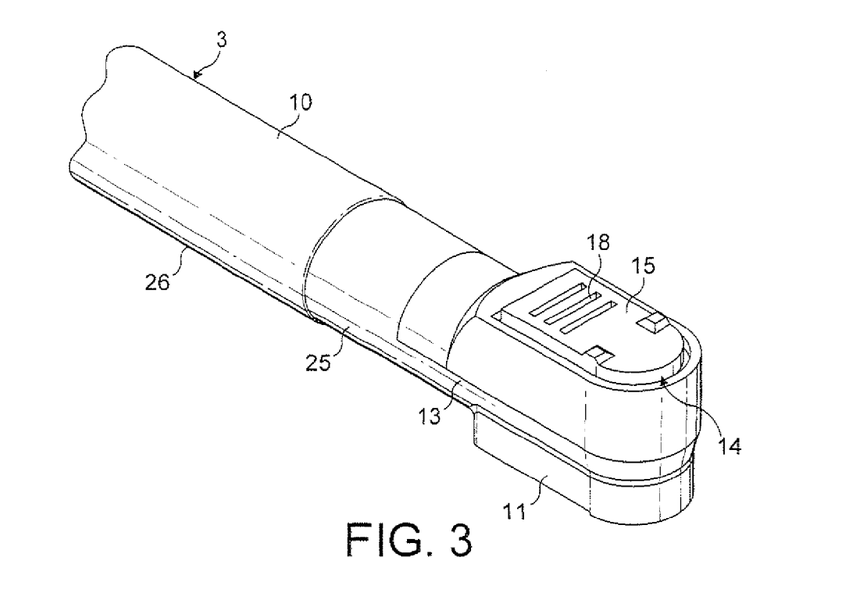
FIG. 3 is a perspective view of the electrosurgical instrument of FIG. 2, shown rotated by 180°.
Figure 4:
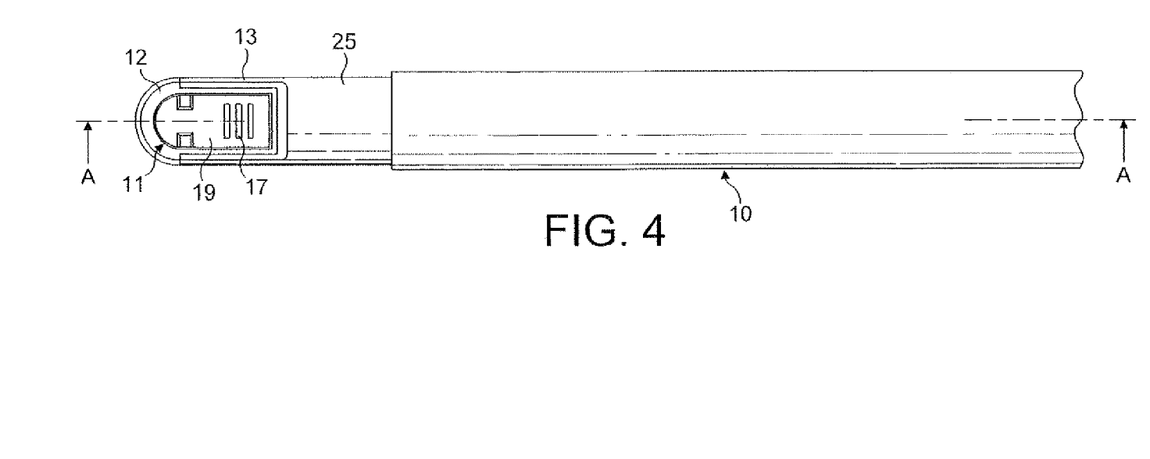
FIG. 4 is a plan view of the electrosurgical instrument of FIG. 2.
Figure 5:
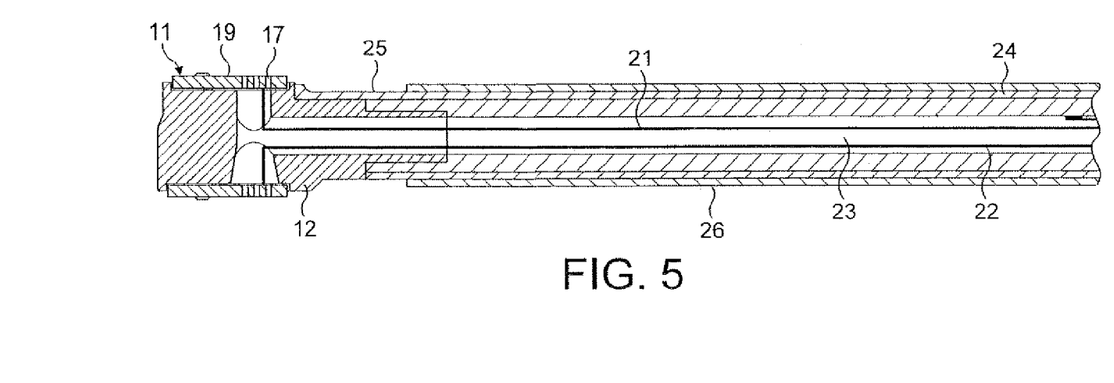
FIG. 5 is a cross-sectional view of the electrosurgical instrument of FIG. 3, taken along the line A-A.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes, or also between the first and second active electrodes, as will be explained shortly.

The handpiece 3 comprises a straight shaft 10 with electrodes at its distal end, as will be described below. FIGS. 2 to 5 show a first tissue treatment electrode 11 mounted on a ceramic insulator 12, the electrode 11 being disposed so that it has an exposed tissue treatment surface 19 presented laterally of the longitudinal axis of the shaft. A second tissue treatment electrode 14 is also mounted on the insulator 12, the electrode 14 being mounted on the opposite lateral side face of the insulator 12. The electrode 14 includes an exposed tissue treatment surface 15, presented laterally of the longitudinal axis of the shaft at 180° to the tissue treatment surface 19. The tissue treatment surface 15 of the second active electrode 14 is of a slightly larger area as compared with the tissue treatment surface 19 of the first active electrode 11. This is to encourage the first active electrode to act as a tissue-vaporisation electrode, and the second active electrode to act as a tissue-coagulation electrode, as will be explained in more detail later. Both tissue treatment electrodes 11 & 14 are formed of tungsten or an alloy of tungsten and platinum.

The first tissue treatment electrode 11 is provided with suction apertures 17, which is in communication with a suction lumen 23 extending along the shaft 10. In order to reduce the problems of vapour bubble production and to assist with the removal of particulate material (such as tissue debris) from the region surrounding the tissue treatment electrode 11, the suction lumen 23 is connected to a suction pump (not shown) which can remove vapour bubbles via the shaft of the instrument through the apertures 17. The second tissue treatment electrode 14 is also provided with suction apertures 18, also in communication with the suction lumen 23.

A return electrode 25 is provided by the distal end portion of the shaft 10, and also includes an extension 13 which overlies the ceramic insulator 12 adjacent the electrodes 11 & 14. The extension 13 is located such that it is closer to the first active electrode 11 as compared with its distance from the second active electrode 14. A polytetrafluoroethylene, a polyolefin, a polyester or ethylene tetrafluoroethylene sleeve 26 surrounds the proximal portion of the shaft 10 adjacent to the return electrode 25. Leads 21, 22 & 24 connect the electrodes 11, 14 & 25 to the RF generator 1 shown in FIG. 1.

The RF generator 1 delivers an electrosurgical current to the instrument 3. The generator 1 includes means for varying the delivered output power to suit different electrosurgical requirements, such as vaporisation or coagulation. The generator is typically as described in our earlier U.S. Pat. No. 6,293,942, with a switching circuit 62 for switching the output lines from the generator to the electrosurgical instrument 3.

Figure 6A:
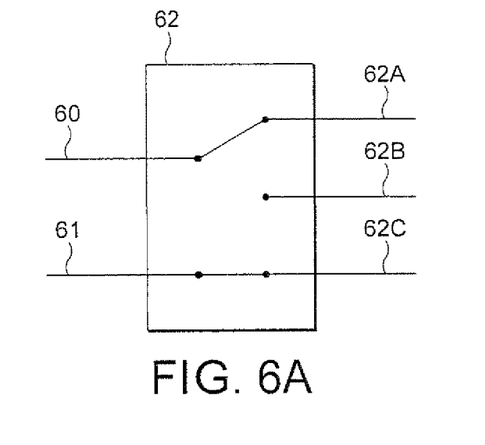
FIGS. 6A & 6B are schematic block diagrams of the output stage of the electrosurgical generator of FIG. 1, shown in different stages of operation.
Figure 6B:
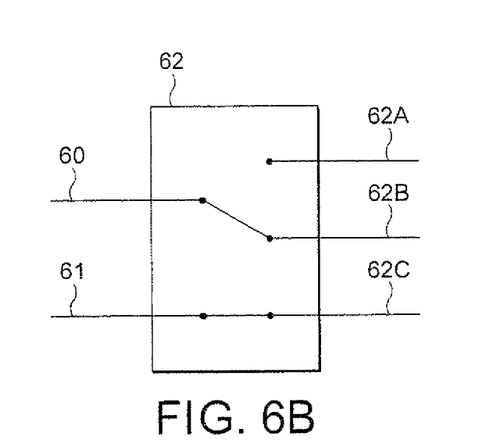

The switching circuit 62 is shown in FIGS. 6A & 6B, and comprises connections 60 & 61 from the generator 1, and output connections 62A, 62B & 62C respectively. Output connection 62A is connected to the first tissue treatment electrode 11 via lead 21, while output connection 62B is connected to the second tissue treatment electrode 14 via lead 22. Similarly, output connection 62C is connected to the third electrode 25, via lead 24. The operation of the electrosurgical system will now be described.

When the user of the system wishes to use the instrument 3 as a cutting instrument, the user sends signals (via the footswitch unit 5 or via the push buttons on the generator) to set the switching circuit 62 into the condition shown in FIG. 6A. In this condition, the connections 60 & 61 from the generator are connected to the output connections 62A & 62C and hence to the first tissue treatment electrode 11 and return electrode 25 respectively. An RF cutting voltage from the generator 1 is supplied to the electrodes 11 & 25 and hence tissue can be vaporised as desired adjacent the tissue treatment surface 19 of the electrode 11. The relatively small separation between the electrode 11 and the extension 13 forming part of the return electrode 25 together with the relatively small surface area of the tissue treatment surface 19 together mean that the bipolar electrode pair is encouraged to fire up into tissue-cutting mode.

Alternatively, when the user of the system wishes to use the instrument 3 as a tissue-coagulating instrument, the user rotates the instrument through 180°, to bring the second active electrode adjacent the tissue to be treated, and sends signals to set the switching circuit 62 into the condition shown in FIG. 6B. In this condition, the connections 60 & 61 from the generator are connected to the output connections 62B & 62C and hence to the second tissue treatment electrode 14 and third electrode 25 respectively. An RF coagulating voltage from the generator 1 is supplied to the electrodes 14 & 25 and hence tissue can be coagulated as desired adjacent the tissue treatment surface 15 of the second active electrode 14. The relatively larger separation between the electrode 14 and the extension 13, together with the relatively larger surface area of the tissue treatment surface 15, means that a substantial area of tissue coagulation is created, and the bipolar electrode pair is discouraged from firing up into tissue-cutting mode.

In this way, the surgeon can change between using the instrument 3 as either a tissue-cutting instrument or as a tissue coagulating instrument merely by operating the footswitch, and by rotating the instrument through 180°. The versatility provided by this arrangement allows for a single instrument effectively to perform the functions of tissue cutting and coagulation, each with an electrode specifically designed for that purpose, without withdrawing the instrument from the surgical site.

The instrument 3 is designed to be operated in a conductive fluid such as saline, with the fluid completing the circuit between the electrodes. However, the instrument 3 can also be used as a dry-field instrument, in which case the user must ensure that the electrodes are placed in contact with the tissue to be treated.

Figure 7:
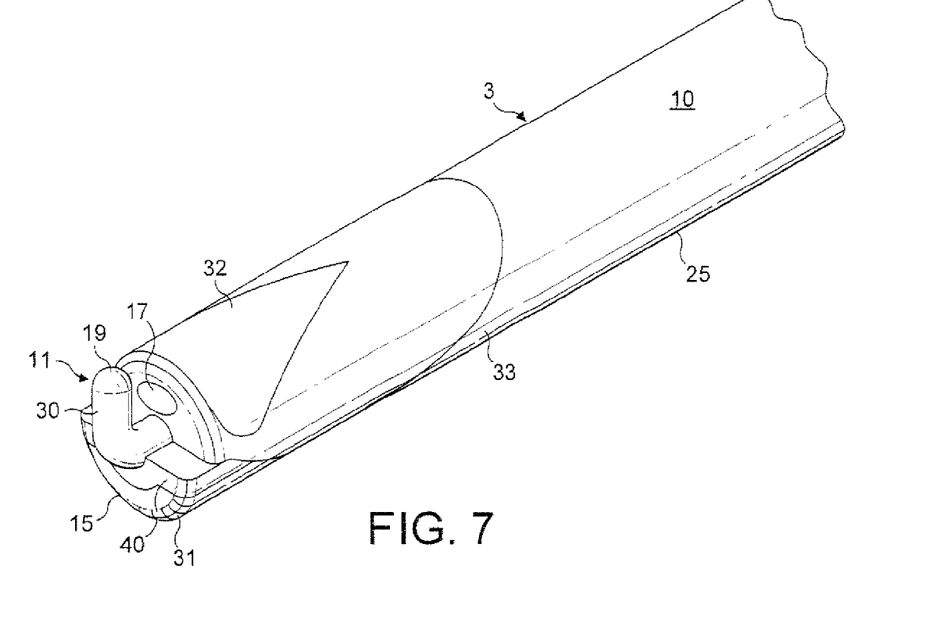
FIG. 7 is a perspective view of an alternative embodiment of electrosurgical instrument in accordance with the invention.
Figure 8:
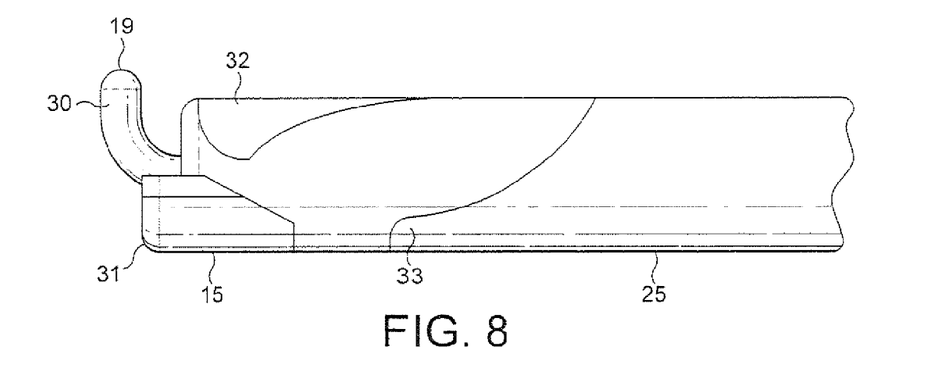
FIG. 8 is a schematic side view of the instrument of FIG. 7.

FIGS. 7 & 8 show an alternative embodiment of handpiece 3, in which the first tissue treatment electrode 11 is in the form of a hook 30 extending from the distal end of the shaft 10. The hook 30 has a laterally-facing tissue treatment surface 19 constituted by the end of the hook. A suction aperture 17 is located on the end face of the shaft, adjacent the hook 30. The second tissue treatment electrode 14 is in the form of a cowl 31 surrounding the bottom part of the distal end of the shaft 10. An insulating member 40 separates the hook 30 from the cowl 31. The cowl 31 has a laterally-facing tissue treatment surface 15, constituted by the curved bottom part of the cowl. The tissue treatment surfaces 19 & 15 are located at 180° with respect to one another, such that they can be used individually depending on the orientation of the shaft.

This handpiece is provided with first and second return electrodes, the first return electrode being in the form of a pad 32 located on the shaft 10 adjacent the upturned portion of the hook 30. The second return electrode is constituted by a metallic sheath 25 carried by the shaft 10. The sheath 25 is provided with a shaped extension 33, extending so as to be adjacent to the cowl 31, The handpiece is designed such that the hook 30 is used for the vaporisation of tissue, while the cowl 31 is used for tissue coagulation. The shape of the hook 30 is obviously very different from that of the cowl 31, with the cowl containing only smooth corners while the hook has a relatively pointed end constituting its tissue treatment surface. The surface area of the cowl 31 is generally greater than that of the hook 30, and the distance between the cowl 31 and the extension 33 is greater than that between the hook 30 and the pad 32. All of these differences help to ensure that when an appropriate electrosurgical voltage is supplied from the generator 1, the hook 30 acts as a tissue vaporising surface while the cowl 31 acts as a tissue coagulating surface.

The operation of the electrosurgical system is very much as described previously, with a switching circuit delivering either an RF vaporising waveform between the hook 30 and the pad 32, or an RF coagulating waveform between the cowl 31 and the extension 33. Depending on whether tissue vaporisation or coagulation is desired, the user of the instrument orients the shaft 10 such that either the end 19 of the hook 30 or the bottom part 15 of the cowl is adjacent the tissue to be treated. As these two tissue treatment surfaces are 180° opposite one another, the shaft must be rotated by the user in order to effect this change.

It will be appreciated that the instrument of FIGS. 7 & 8 uses two separate return electrodes 32 & 25, whereas the instrument of FIGS. 2 to 5 uses a single return electrode 25 for both active electrodes 11 & 14. It therefore follows that the switching circuit of FIGS. 6A & 6B will need to be modified in order to encompass the additional return electrode, but this is well within the capability of those skilled in the art of electrosurgical generator design.

Figure 9:
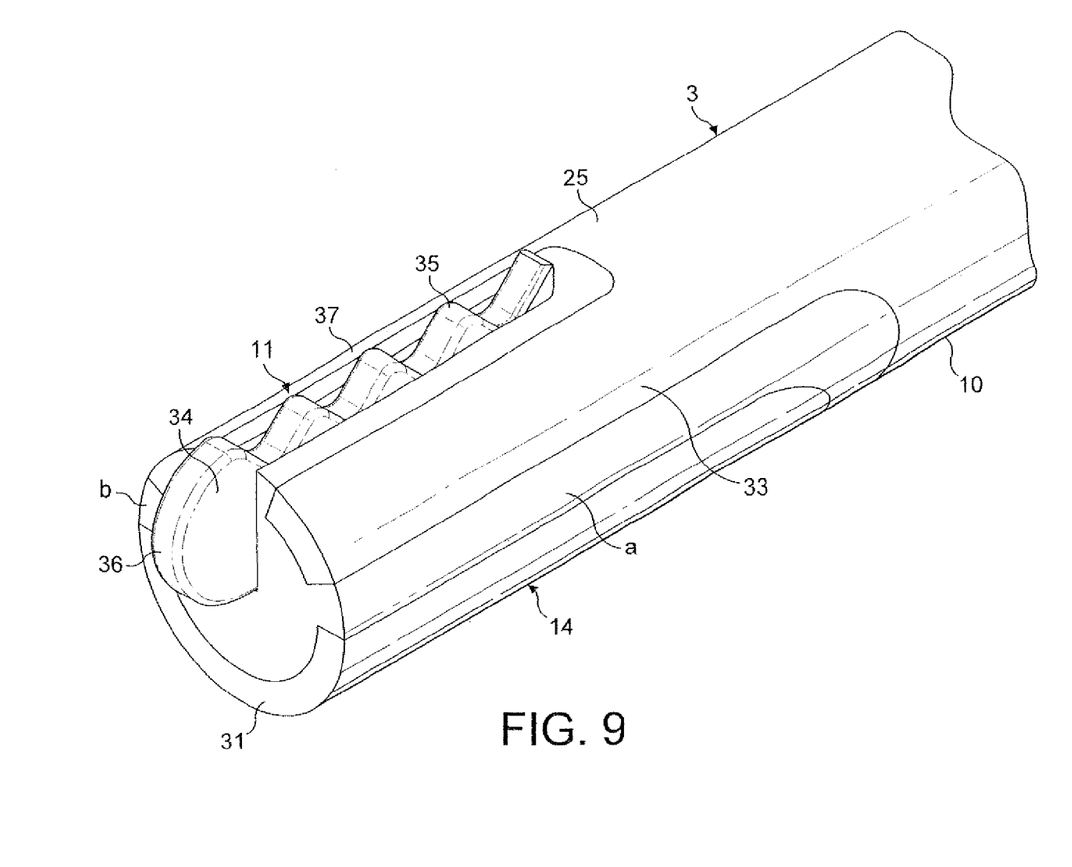
FIG. 9 is a perspective view of a further embodiment of electrosurgical instrument in accordance with the invention.

FIG. 9 shows a further alternative embodiment of handpiece 3, in which the first tissue treatment electrode 11 is in the form of a blade 34, extending both laterally of the shaft at 35 and also from the distal end of the shaft at 36. The second tissue treatment electrode 14 is in the form of a cowl 31 located on the shaft 10 at 180° to the blade 34. A single return electrode is provided by a metallic sheath 25 located on the shaft 10 as previously described, but the sheath 25 has not one but two extensions 33 & 37. Extension 33 extends alongside the blade 34, and lies between the blade and the cowl 31 on one side thereof. Extension 37 extends alongside the blade 34 on the opposite side thereof, and lies between the blade and the cowl on the opposite side to that of the extension 33.

The operation of the handpiece of FIG. 9 will now be described, and it can be used in different modes of operation. In a first mode of operation, the instrument is used to vaporise tissue using the blade 34. The instrument is maneuvered such that the blade 34 is adjacent the tissue to be treated, and an RF vaporising waveform is provided by the generator 1 between the blade 34 and the return electrode 25. Tissue will be vaporised in the area surrounding the blade 34, and particularly in the area between the blade 34 and the extensions 33 & 37 on either side thereof.

In a second mode of operation, the instrument is used to coagulate tissue using the cowl 31. The handpiece 3 is maneuvered such that the cowl 31 is adjacent the tissue to be treated, and the generator 1 supplies an RF coagulating waveform between the cowl 31 and the return electrode 25. Tissue will be coagulated in the region of the cowl 31, and in particular in the region "a" between the cowl 31 and the extension 33, and region "b" between the cowl 31 and the extension 37. The shaft 10 can be oriented such that only region "a" or region "b" is adjacent tissue to be treated, or for bulk tissue coagulation, both regions can be employed simultaneously. As region "a" is radially offset by 90° from the cutting blade 34 in one radial direction, and region "b" by 90° in the opposite direction, the shaft 10 can be rotated to bring either region into contact with tissue to be treated.

In a further mode of operation, the switching circuit illustrated in FIGS. 6A & 6B is rapidly alternated between the situation shown in FIG. 6A and that in FIG. 6B. This sort of arrangement, described in more detail in our earlier U.S. Pat. No. 6,966,907, provides a blended output in which a blend of RF vaporisation and coagulation voltages is provided by the generator, with the RF cutting voltage being supplied to one pair of electrodes (such as electrodes 34 & 25) and the RF coagulation voltage being supplied to the other pair of electrodes (such as electrodes 31 & 25). In this way the instrument is capable of simultaneous vaporisation and coagulation of tissue. Referring to FIG. 9, the blended RF output is supplied to the handpiece 3, and the instrument is oriented by the user such that it is transcribed across the tissue to be treated, with first the blade 34 and then the region "a" (or region "b", depending on which direction the instrument is moved) coming into contact with the tissue. The blade 34 vaporises the tissue as it passes over it, quickly followed by the region "a", which causes the remaining tissue to be coagulated, thereby reducing any bleeding caused by the vaporisation of tissue by the blade 34. In this way, the instrument is capable of selected tissue vaporisation, tissue coagulation, or a simultaneous combination of both vaporisation and coagulation, each requiring a different radial orientation of the shaft 10.

Alternative embodiments will be envisaged by those skilled in the art without departing from the scope of the present invention. For example, the electrosurgical instrument can also be used for delivering a blended power output, to whichever pair of electrodes is selected as opposed to different electrode pairs as described above. This is achieved by automatically alternating the output of the RF generator 1 between the coagulation and vaporisation power levels, so that more haemostasis is produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the coagulation mode. This produces a less aggressive tissue vaporisation than occurs in the vaporisation mode, with a consequent reduction in both bubble formation and the risk of tissue charring.

The invention claimed is:

1. An electrosurgical instrument including an instrument shaft having a longitudinal axis and an electrode assembly at one end of the shaft, the electrode assembly consisting of:
   a first, single active electrode, which is not part of any array of electrodes, the array of electrodes being defined as a plurality of electrodes which are disposed on a same surface of or at a same radial position on any instrument shaft,
   a second, single active electrode, which is separate from the first electrode and which is not part of the any array of electrodes, and one or more return electrodes, at least a portion of the one or more return electrodes being set back along the longitudinal axis of the instrument with respect to the first active electrode, each of the electrodes being electrically insulated from one another by means of one or more insulation members, the first and second active electrodes each having an exposed surface for treating tissue, the first and second active electrodes each having a different characteristic, in that the distance between the first active electrode and the nearest return electrode is less than that between the second active electrode and the nearest return electrode, such that the first active electrode tends to act as a vaporisation electrode and the second active electrode tends to act as a coagulation electrode, the exposed surface of the first active electrode being positioned so as to treat tissue disposed laterally of the instrument shaft at a first radial position with respect to the longitudinal axis of the instrument shaft, the exposed surface of the second active electrode being positioned so as to treat tissue disposed laterally of the instrument shaft at a second radial position with respect to the longitudinal axis of the instrument shaft, the first and second radial positions being separated by an angle of at least 30°, the instrument further including:

a switch, and a switching circuit, which when the switch is manually set to a first position, activates a first set of connections by which the first active electrode is placed in circuit with one of the one or more return electrodes, such that in use a current path is established between the first active electrode and at least one return electrode, and which when the switch is manually set to a second position, activates a second set of connections by which the second active electrode is placed in circuit with one of the one or more return electrodes, such that in use a current path is established between the second active electrode and at least one return electrode.

2. The electrosurgical instrument according to claim 1, wherein the first and second radial positions are separated one from another by at least 45°.

3. The electrosurgical instrument according to claim 2, wherein the first and second radial positions are separated one from another by at least 90°.

4. The electrosurgical instrument according to claim 3, wherein the first and second radial positions are separated one from another by approximately 180°.

5. The electrosurgical instrument according to claim 1, wherein the difference in characteristic between the first and second active electrodes is also that the surface area of the first active electrode is less than that of the second active electrode.

6. The electrosurgical instrument according to claim 1, wherein the difference in characteristic between the first and second active electrodes is that the shape of the first active electrode is different from that of the second active electrode.

7. The electrosurgical instrument according to claim 1, wherein at least a portion of the one or more return electrodes is axially set back with respect to the second active electrode.

8. The electrosurgical instrument according to claim 7, wherein at least one of the one or more return electrodes is in the form of a radial band around the instrument shaft.

9. The electrosurgical instrument according to claim 1, wherein the exposed tissue treatment surface of the first active electrode is substantially planar.

10. The electrosurgical instrument according to claim 1, wherein the exposed tissue treatment surface of the second active electrode is substantially planar.

11. The electrosurgical instrument according to claim 1, including a suction lumen extending along the length of the shaft.

12. The electrosurgical instrument according to claim 11, wherein the first active electrode is provided with at least one aperture in communication with the suction lumen.

13. The electrosurgical instrument according to claim 11, wherein the second active electrode is provided with at least one aperture in communication with the suction lumen.

14. The electrosurgical instrument according to claim 1, wherein the one or more return electrodes comprises a first return electrode and a second return electrode, and the first set of connections are such that the first active electrode can be placed in circuit with the first return electrode such that in use a current path is established between the first active electrode and the first return electrode, and the second set of connections are such that the second active electrode can be placed in circuit with the second return electrode such that in use a current path is established between the second active electrode and the second return electrode.

15. An electrosurgical system including an electrosurgical instrument and an electrosurgical generator, the electrosurgical instrument including an instrument shaft having a longitudinal axis and an electrode assembly at one end of the shaft, the electrode assembly consisting of:

a first, single active electrode, which is not part of any array of electrodes, the array of electrodes being defined as a plurality of electrodes which are disposed on a same surface of or at a same radial position on any instrument shaft, and a second, single active electrode, which is separate from the first electrode and which is not part of the any array of electrodes, and one or more return electrodes, at least a portion of the one or more return electrodes being set back along the longitudinal axis of the instrument with respect to the first active electrode, each of the electrodes being electrically insulated one from another by means of one or more insulation members, the first and second active electrodes each having an exposed surface for treating tissue, the exposed surface of the first active electrode being positioned so as to treat tissue disposed laterally of the instrument shaft at a first radial position with respect to the longitudinal axis of the instrument shaft, the exposed surface of the second active electrode being positioned so as to treat tissue disposed laterally of the instrument shaft at a second radial position with respect to the longitudinal axis of the instrument shaft, the first and second radial positions being separated by an angle of at least 30°, a distance between the first active electrode and the nearest return electrode being less than that between the second active electrode and the nearest return electrode, such that the first active electrode tends to act as a vaporisation electrode and the second active electrode tends to act as a coagulation electrode, the instrument further including:

a first set of connections by which the first active electrode can be placed in circuit with one of the one or more return electrodes, such that in use a current path is established between the first active electrode and at least one return electrode, and a second set of connections by which the second active electrode can be placed in circuit with one of the one or more return electrodes, such that in use a current path is established between the second active electrode and at least one return electrode, the electrosurgical generator including:

a source of radio frequency energy capable of producing either a coagulating RF waveform or a cutting RF waveform, the cutting RF waveform being different from the coagulating RF waveform, first and second output connections connected to the first and second active electrodes, respectively, a third output connection connected to the one or more return electrodes of the electrosurgical instrument, a switch, and a switching circuit, which when a cutting RF waveform is selected using the switch, directs the cutting RF waveform between the first and third output connections and hence the first active electrode and at least one return electrode, and which when a coagulating RF waveform is selected using the switch, the switching circuit directs the coagulating RF waveform between the second and third output connections and hence the second active electrode and at least one return electrode.

16. The electrosurgical system according to claim 15, wherein the first and second active electrodes each have a different characteristic.

17. The electrosurgical system according to claim 15, wherein the switch comprises a footswitch.

18. The electrosurgical system according to claim 17, wherein the switch comprises a handswitch carried on the electrosurgical instrument.

19. The electrosurgical system according to claim 15, wherein the switching circuit is a part of the generator.

20. The electrosurgical system according to claim 15, wherein the switching circuit is a part of the electrosurgical instrument.

21. The electrosurgical system according to claim 15, wherein the generator and electrosurgical instrument are such that the instrument is designed to be operated in a conductive fluid, with the conductive fluid completing the current path between the electrodes.

22. The electrosurgical system according to claim 15, wherein the generator and electrosurgical instrument are such that the instrument is designed to be operated in a dry-field environment, with the electrodes being in direct contact with the tissue to be treated, and with the tissue completing the current path therebetween.

* * * * *